United States Patent [19]

Gross

[11] Patent Number: 5,403,870
[45] Date of Patent: Apr. 4, 1995

[54] PROCESS FOR FORMING A POROUS PARTICLE OF AN ABSORBENT POLYMER

[75] Inventor: James R. Gross, Appleton, Wis.

[73] Assignee: Kimberly-Clark Corporation, Neenah, Wis.

[21] Appl. No.: 124,732

[22] Filed: Sep. 20, 1993

Related U.S. Application Data

[60] Division of Ser. No. 662,518, Feb. 28, 1991, abandoned, which is a continuation of Ser. No. 359,470, May 31, 1989, abandoned.

[51] Int. Cl.$^6$ .............................. C08J 9/26; C08J 9/28
[52] U.S. Cl. ..................................... 523/105; 521/62; 521/64; 521/88; 521/142
[58] Field of Search .................... 523/105; 521/62, 64, 521/88, 142, 149

[56] References Cited

U.S. PATENT DOCUMENTS

| | | | |
|---|---|---|---|
| 3,073,309 | 1/1963 | Mosier | 128/290 |
| 3,121,427 | 2/1964 | Mosier | 128/284 |
| 3,901,236 | 8/1975 | Assarsson et al. | 128/284 |
| 3,902,497 | 9/1975 | Casey | 128/296 |
| 3,939,105 | 2/1976 | Jones, Jr. et al. | 260/2.5 AY |
| 4,002,173 | 1/1977 | Manning et al. | 128/296 |
| 4,059,552 | 11/1977 | Zweigle et al. | 260/29.6 TA |
| 4,093,776 | 6/1978 | Aoki et al. | 428/402 |
| 4,172,066 | 10/1979 | Zweigle et al. | 260/29.6 TA |
| 4,192,784 | 3/1980 | Brown et al. | 260/8 |
| 4,212,302 | 7/1980 | Karami | 128/287 |
| 4,286,341 | 9/1981 | Greer et al. | 3/1.4 |
| 4,446,261 | 5/1984 | Yamasaki et al. | 524/40 |
| 4,473,611 | 9/1984 | Haq | 428/198 |
| 4,529,739 | 7/1985 | Scott et al. | 521/72 |
| 4,606,958 | 8/1986 | Haq et al. | 428/68 |
| 4,611,014 | 9/1986 | Jomes et al. | 521/146 |
| 4,612,334 | 9/1986 | Jones et al. | 521/146 |
| 4,622,036 | 11/1986 | Goodrum | 604/367 |
| 4,647,636 | 3/1987 | Makita et al. | 526/206 |
| 4,666,975 | 5/1987 | Yamasaki et al. | 524/733 |
| 4,685,915 | 8/1987 | Hasse et al. | 604/378 |
| 4,703,067 | 10/1987 | Mikita et al. | 521/63 |
| 4,742,086 | 5/1988 | Masamizu et al. | 521/62 |
| 4,795,762 | 1/1989 | Diamantoglou et al. | 521/84.1 |
| 4,997,425 | 3/1991 | Shioya et al. | 604/304 |

OTHER PUBLICATIONS

"Scanning Methods in Quantitative Metallography" from *Quantitative Microscopy* by H. F. Fischmeister; pp. 336–348.

Primary Examiner—Paul R. Michl
Assistant Examiner—LaVonda R. DeWitt
Attorney, Agent, or Firm—Thomas J. Mielke

[57] ABSTRACT

A porous structure of a water-swellable, water-insoluble polymeric material which porous structure possesses improved free swell capacity and is able to demonstrate said improved free swell capacity when in contact with an absorbent material such as a cellulosic fibrous web. Also disclosed is a method of making such a porous polymeric structure. The method comprising the steps of forming an oil-in-water suspension, wherein the water phase contains a water-soluble monomer and a crosslinking agent and the oil phase is a volatile organic compound having a boiling point greater than the boiling point of water. The monomer present in the water phase is polymerized to form a polymeric material having dispersed therein the oil phase. The resultant polymeric material is then dried at a temperature above the boiling point of water, such that the volatile organic compound volatilizes thereby forming pores in the polymeric material, which pores have a diameter of at least about 20 microns. The polymeric material is at least partially dried before the organic compound volatilizes so that the polymeric material possesses sufficient structural integrity to maintain the openness of the chambers.

8 Claims, 3 Drawing Sheets

PROCESS FOR FORMING A POROUS PARTICLE OF AN ABSORBENT POLYMER

This is a divisional application of copending application Ser. No. 07/662,518, filed on Feb. 28, 1991, which in turn is a continuation application of U.S. patent application Ser. No. 07/359,470, filed May 31, 1989, now abandoned.

BACKGROUND OF THE INVENTION

1. Field of the Invention

The present invention relates to water-swellable, water-insoluble polymeric materials. Specifically, the present invention concerns a porous structure formed from a water-swellable, water-insoluble polymeric material.

2. Background of the Related Art

Water-swellable, water-insoluble polymeric materials, commonly known as superabsorbents, are known for use in a variety of applications. For example, it is known to incorporate such water-swellable polymeric materials into absorbent products such as, diapers, sanitary napkins, bandages, adult incontinence products and the like.

When water-swellable polymeric materials are incorporated into personal care products such as diapers, the water-swellable polymeric materials are often present within and carried by a fibrous web. The fibrous web carrying the super absorbent material forms the absorbent core of such personal care products. The water-swellable polymeric materials are present within the fibrous web in order to increase the absorbent capacity of the fibrous web. In this manner, a smaller absorbent core can be employed in the personal care product since the composite of fiber and water-swellable polymer has a greater absorbency per unit volume. Unfortunately, water-swellable polymeric materials are generally substantially more expensive than the fibrous webs in which they are located. Accordingly, in order to minimize the cost of the absorbent core, it is generally desirable to utilize the water-swellable polymeric material to its greatest extent and to employ a water-swellable polymeric material having the greatest possible capacity while still maintaining other desirable properties such as, gel strength, the ability to absorb and retain fluid against an applied pressure, and the like.

Attempts have been made to increase the water absorbing properties of water-swellable polymeric materials to improve their performance and thereby, minimize the amount of water-swellable polymer present in an absorbent structure. Such an attempt is described by Masamizu et al. in U.S. Pat. No. 4,742,086, issued May 3, 1988. Masamizu et al. describes a process for manufacturing porous polymer and the porous polymer formed by the process. The process described by Masamizu comprises the steps of:

1. Forming an O/W emulsion wherein the inner phase of the O/W emulsion is a hydrophobic phase and the outer phase thereof is a water phase containing at least one water soluble polymerizable monomer;

2. Adding the O/W emulsion to a hydrophobic dispersing medium containing an oil-soluble surfactant to form an O/W/O emulsion; and 3. Polymerizing the monomer. The processes is described as producing a polymer having a porous structure.

As used by Masamizu et al. the term "porous" refers to a polymer having internal voids which internal voids are not connected to the surface of the polymer particles. The outer surface of the polymer particles has a pitted appearance. The type of porous particles formed by Masamizu et al. is clearly described in FIGS. 2 and 3 of Masamizu et al. The porous particles described by Masamizu et al. are claimed to have superior initial water-absorbing speed and improved capacity under pressure.

Similarly, U.S. Pat. No. 4,795,762 issued Jan. 3, 1989 to Diamantoglou, et al. is directed to a water-swellable composition having a spongy structure. The composition is described as having a high swelling capacity and swelling rate.

U.S. Pat. No. 4,703,067 issued Oct. 27, 1987 to Mikita et al. is directed to a process for preparing a dry, solid water absorbing polyacrylate resin. The process described by Mikita et al. involves forming a monomer mixture of potassium acrylate, a polyvinyl monomer, and water, said monomer mixture comprising 55 to 80 weight percent monomers based on total monomer mixture weight. The monomer mixture may contain up to 15 weight percent of a non-aqueous solvent having a boiling point between 40° and 150° C. A polymerization initiator is added to the monomer mixture and the mixture polymerized while using the exothermic heat of reaction to drive water away from the acrylate resin.

The solvents described by Mikita et al. may be water miscible, e.g., ethanol, methanol and the like, or water immiscible, e.g., benzene, toluene, tetrahydrofuran, and the like. The polyacrylates produced when the nonaqueous solvents are present are found to possess quicker absorption rates but not to possess higher absorption capacities at 15 minutes, see for example Tables 6 and 7. Mikita et al. does not describe the physical characteristics of the polyacrylate resin formed by the described process.

The formation of porous particles of polymeric material is known in connection with non water-swellable polymeric materials. For example, U.S. Pat. No. 4,611,014 issued Sep. 9, 1986 and U.S. Pat, No. 4,612,334 issued Sep. 16, 1986, both patents being issued to Jones et al., are directed to porous polymers. The polymers described by Jones et al. are highly porous cross-linked functionalized polymers having interconnected cavities and a pore volume greater than 5.6 cubic centimeters per gram. The polymers are generally based on styrene and/or acrylate compositions. The porous polymers described by Jones et al. have interconnected cavities or chambers of micron dimensions.

SUMMARY OF THE INVENTION

It is desirable to produce a porous water-swellable, water-insoluble, polymeric material which polymeric material possesses improved absorption capacity. Additionally, it is desired to provide a process by which such porous water-swellable, water-insoluble polymeric materials can be efficiently produced. It is to these and other related goals that the present invention is directed.

The present invention concerns, in one aspect, a process for forming a porous water-swellable water-insoluble polymeric material. The process comprises the steps of forming an oil-in-water suspension, the water phase containing at least one water-soluble monomer and a crosslinking agent. The oil phase comprises a volatile organic compound having a boiling point greater than the boiling point of water. The monomer present in the water phase is polymerized to form a water-swollen water-insoluble polymeric material having dispersed therein an amount of the oil phase. The water-swollen, water-insoluble polymeric material is then dried at a temperature above the boiling point of the water, such that the volatile organic compound present within the polymeric material volatilizes after the polymeric material has at least partially dried. As the volatile organic compound volatilizes it creates pores in the polymeric structure. The pores generally have a diameter greater than at least about 20 microns.

In the second aspect, the present invention concerns a porous structure comprising a water-swellable, water-insoluble polymeric material. The porous structure defines a plurality of chambers (pores), which chambers are in open communication with an outer surface of the structure of polymeric material and, thus, the ambient atmosphere. The chambers have a diameter of at least about 20 microns.

DETAILED DESCRIPTION OF THE PREFERRED EMBODIMENTS

Figure 1:
FIGS. 1 and 2 are photomicrographs of nonporous water-swellable polymer particles representative of known polymeric materials.

In one aspect, the present invention relates to a water-swellable, water-insoluble polymeric material which possesses improved absorbent capacity as a result of being porous. As used herein, the term "porous" refers to a series of chambers or pores (hereinafter used interchangeably) present in the polymeric material, which pores are in open communication with the surface of the particles and, thus, the ambient atmosphere and which pores serve to increase the thirty (30) minute free swell capacity of the polymeric material in a one percent (1%) saline solution. The pores have a diameter of at least about 20 microns. Due to the fact that the pores present in the polymeric materials of the present invention are in open communication with the ambient atmosphere, when the polymeric materials of the present invention are placed in a liquid environment, the liquid can flow into the pores with relative ease.

The term "porous" is not intended to encompass a polymeric material which is primarily possessed of voids within its interior, which voids are not in open communications with the ambient atmosphere.

The water-swellable, water-insoluble polymeric material suitable for use in the present invention is generally known to those skilled in the art as superabsorbent polymer. Any water-swellable, water-insoluble polymeric material capable of absorbing at least about ten (10) times its own weight in water is believed suitable for use in the present invention. Exemplary of known water-swellable, water-insoluble polymers are those polymers formed from alkali metal and ammonium salts of acid-group containing monomers, such polymers include polyacrylic acid, polymethacrylic acid, maleic anhydride copolymers, poly vinyl sulfonates, carboxymethyl cellulose, hydrolyzed acrylonitrile grafted starch, acrylic acid grafted starch; polyvinyl alcohol; hydroxyethyl cellulose; hydroxypropyl cellulose; polyvinyl pyrrolidone; polyvinyl pyridine; polyvinyl morpholinone; and copolymers or mixtures thereof. Processes for preparing water-swellable polymeric materials are known to those skilled in the art.

As a general rule, the water-swellable polymeric materials are prepared by polymerizing one or more monomers which, if homopolymerized by conventional methods would form water-soluble polymers. To render them water-swellable and water-insoluble, the polymers or mixtures of polymers are typically reacted, frequently with a crosslinking agent to form crosslinked polymers, thereby introducing a limited water-insolubility while retaining susceptibility to swelling in water and water-containing fluids.

The porous nature of the water-swellable polymeric materials of the present invention has been found to provide the water-swellable polymeric materials with increased absorbent capacity and increased absorption rates. As used herein, absorbent capacity is expressed in terms of the grams of liquid absorbed per gram of polymeric material in 30 minutes. Thus, reference to increased absorbent capacity of the porous polymers of the present invention indicates that the porous water-swellable polymers can absorb more liquid per gram of polymer than the identical non-porous water-swellable polymeric material. It is generally preferred that the porous polymers of the present invention have a free swell capacity after thirty (30) minutes in a one percent (1%) aqueous sodium chloride solution which is at least about ten percent (10%), preferably about thirty percent (30) greater than the same polymer in a non-porous state. Additionally, it is beneficial if the porous polymers have a free swell capacity after 30 minutes in a 1% aqueous sodium chloride solution of at least about 10, preferably about 20, and more preferably about 30 grams of liquid per gram of polymer.

As discussed above, a majority of the chambers present in the polymeric materials of the present invention have a diameter of at least about 20 microns, preferably of at least about 30 microns, more preferably of at least about 50 microns. It is similarly beneficial if a majority of the chambers present in the polymeric material have a diameter which is less than about 150 microns, preferably less than about 100 microns, more preferably less than about 75 microns.

The polymeric materials of the present invention are well suited for use in absorbent products such as diapers, incontinence garments, sanitary napkins, bandages, and the like. When the polymeric materials of the present invention are, for example, to be incorporated into a diaper, the polymeric materials will generally be in particulate form and will be located within and carried by a fibrous web. The particles will generally have a size such that they are passed by a 20 mesh screen and retained by a 100 mesh screen (150–800 microns). The porous polymeric particles of the present invention may be used, in such absorbent products, either alone or in combination with particles of non-porous polymeric material. The fibrous web can, for example, be made from cellulosic fibers such as wood pulp fluff. As a general rule the diaper will comprise an outer water-impervious liner, an absorbent core comprising a fibrous web containing the porous water-swellable polymeric materials of the present invention adjacent to one surface of the outer liner, and a water-pervious body side liner adapted to contact the skin of the wearer, which body side liner is adjacent to a surface of the absorbent core. This is, the fibrous web is sandwiched between said outer liner and said body side liner. Such products are generally described in U.S. Pat. Nos. 4,710,187, issued Dec. 1, 1987, to Boland et al.; 4,762,521, issued Aug. 9, 1988, to Roessler, et al.; 4,770,656, issued Sep. 13, 1988, to Proxmire, et al.; and 4,798,603, issued Jan. 17, 1989 to Meyer et al., which references are hereby incorporated by reference.

In a second aspect, the present invention concerns a process for forming the porous water-swellable, water-insoluble polymeric materials of the present invention. Generally, the porous polymeric materials of the present invention are formed through a suspension polymerization process. The process involves forming an oil-in-water suspension, wherein the water phase contains at least one water-soluble monomer and a crosslinking agent. The oil phase comprises a volatile organic compound having a boiling point greater than the boiling point of water. The monomer present in the water phase is polymerized to form a water-swollen, water-insoluble polymeric gel material having dispersed therein discrete drops of the volatile organic compound (oil phase). The water-swollen water-insoluble polymeric gel material is dried at a temperature above the boiling point of water such that the volatile organic compound volatilizes to form the pores of the polymeric material of the present invention.

Exemplary of water-soluble monomers suitable for use in the present invention are vinyl monomers having a polymerizable unsaturated group, such as an olefin unsaturated carboxylic acid, olefin unsaturated sulfonic acid, olefin unsaturated amine or olefin unsaturated ether. Among these, examples of vinyl monomers having a sulfonic group include unsaturated sulfonic acids, such as acryl amido methyl propane sulfonic acid, allyl sulfonic acid, and examples of vinyl monomers having amino groups include and unsaturated amines such as dimethyl aminoethyl methacrylate. Examples of vinyl monomers having carboxyl groups include unsaturated carboxylic acids, such as acrylic acid, methacrylic acid, maleic acid, and fumaric acid. Furthermore, water-soluble salts of these monomers may be employed. Exemplary of such salts are the salts of acrylic acid, methacrylic acid or the like, including the alkali metal salts, and ammonium salts of unsaturated carboxylic acids. Additionally, it should be noted that the above described water-soluble monomers can be employed in conjunction with limited quantities (less than about 10 weight percent, based on total monomer weight) of a water-insoluble monomer which is copolymerizable with the water-soluble monomers. Exemplary of water-insoluble monomers which may be employed are the alkyl ($C_1$-$C_{18}$) unsaturated carboxylic acid esters, such as acrylate, methacrylate, maleate and fumarate.

The water-soluble monomer is dissolved in an aqueous phase in concentrations within the range of from about 15 to about 50 weight percent based on total weight of the water. At concentrations greater than about 50 weight percent the polymer formation becomes more complicated and control of the pore size becomes more difficult.

A crosslinking agent, e.g., a di or poly functional comonomer is then added to the monomer/water solution. The crosslinker is generally added in an amount of from about 0.01 to about 5.0 weight percent based on total weight of the monomer employed. Any crosslinking agent capable of crosslinking the water-soluble monomer as it polymerizes or, in some instances, after the polymer has formed is suitable for use in the present invention.

Exemplary or suitable crosslinking agents are polyallyl compounds, such as N,N'-diallyl acrylamide, diallylamine, diallyl methacrylamide, diallyl phthalate, diallyl malate, diallyl terephthalate, triallylamine, triallyl cyanurate and triallyl phosphate; polyvinyl compounds such as divinylbenzene, trimethylolpropane triacrylate, N,N'-methylenebisacrylamide, ethylene glycol diacrylate, ethylene glycol dimethacrylate and glycerin trimethacrylate; polyglycidyl ethers such as ethyleneglycol glycidyl ether and polyethylene glycoldiglycidyl ether; haloepoxy compounds such as epichlorohydrin and methylchlorohydrin; polyaldehydes such as glutaraldehyde and glyoxal; and inorganic salts or organic metal salts which generate polyhydric ions such as calcium, magnesium, zinc and aluminum.

The crosslinking agent is added in an amount selected in accordance with the properties which it is intended to impart to the final product. Those skilled in the art will recognize that increasing the amount of crosslinking agent present correspondingly increases the amount of crosslinking within the polymeric material. Increasing the crosslinking within the polymeric material controls the water-swellability of the polymeric material and therefore its absorbent capacity and gel strength.

To the aqueous phase containing monomer and crosslinking agent is added a suspending or dispersing agent capable of suspending the oil phase in the aqueous phase. Those skilled in the art will recognize suitable suspending agents for use in the present invention. Exemplary of such suspending agents are the water-soluble high-molecular dispersants such as polyvinylalcohols whose saponification value is 60–95 mole percent and whose polymerization degree is 100–3000, modified polyvinyl alcohols in which one or more sulfonic groups or carboxylic groups are incorporated in polyvinyl alcohol, polyethyleneoxide, hydroxyethylcellulose, gum arabic and the like.

The suspending agent is present in an amount suitable to achieve the desired degree of suspension of the oil in the aqueous phase. Generally, the suspending agent is present in an amount of from about 0.1 to about 2.0, preferably from about 0.2 to about 1.0 weight percent based on total weight of the aqueous phase.

The oil phase is then dispersed in the aqueous phase. The oil phase is suitably a volatile organic compound having a boiling point greater than the boiling point of water. As described above, the chambers of the polymeric material according to the present invention are formed by volatilizing the volatile organic compound after at least partially drying the water-swollen polymeric material formed during the polymerization process. Thus, it is necessary for the volatile organic compound to have a boiling point greater than the boiling point of water so that the organic compound does not volatilize until a degree of drying has occurred in the polymer. That is, until a portion of the water present in the water-swollen polymeric material has been evaporated. It is similarly desired that the volatile organic compound have a boiling point below the temperature at which the polymeric material melts or degrades.

The chambers are formed when the organic compound volatilizes. As the organic compound volatilizes (changes from liquid to gas) it expands such that it blows a hole in the polymeric material and is released to the atmosphere. It is important that the polymeric material be dried to a state sufficient so that the polymeric material does not collapse thus closing the chamber created by the volatilization of the organic compound. If the organic compound volatilizes before the polymeric material is at least partially dried, the polymeric material lacks sufficient strength to keep the chamber formed by the volatilization open.

Exemplary of the volatile organic compound suitable for use in the present invention are toluene; 1-butanol; 1,1-dimethylcyclohexane; and octane.

Clearly, the amount of the volatile organic compound incorporated into the aqueous phase determines the degree of porosity present in the final polymeric material. Similarly, the size of the pores present in the polymeric material is dependent on the size of the oil phase droplets suspended in the aqueous phase. This in turn depends in part upon the amount and type of suspending agent chosen and the degree of agitation or mixing to which the oil-in-water suspension is subjected. Those skilled in the art will recognize suitable parameters for the above described variables. The optimum values for the variables can easily be experimentally determined to produce the required degree of porosity and the desired pore size distribution. As a general rule, the volatile organic compound will be added to the aqueous phase in an amount below that at which phase inversion occurs. As a general rule, the volatile organic compound will be added to the aqueous phase in an amount from about 20 to about 40 preferably from about 25 to about 35 weight percent based on total weight of the oil-in-water suspension.

The water-soluble monomer is then polymerized. Polymerization generally occurs through a free radical process and can be initiated by known free radical polymerization initiators. Exemplary polymerization initiators include the ketone peroxides, such as methyl ethyl ketone peroxide and methyl isobutyl ketone peroxide; dialkyl peroxides such as di-tert-butyl peroxide and tert-butyl cumyl peroxide; alkyl peresters such as tert-butyl acetate and tert-butyl perisobutylate; peroxides such as hydrogen peroxide; persulfates, such as sodium persulfate, potassium persulfate and ammonium persulfate; and azo-compounds, such as 2-carbamoylazo-isobutyronitrile, 2, 2'-azobis (N,N'-dimethyleneisobutylamidine) dihydrochloride, 2, 2'-azobis (2-amidinopropane) dihydrochloride, 2, 2'-azobis (NN'-dimethyleneisobutylamidine), 4, 4'-azobis (4-cyanopentanoic acid) azobis isobutyronitrile, 2, 2'-azobis (4-methoxy-2, 4-dimethylvaleronitrile), (1-phenylethyl) azodiphenylmethane, 2, 2'-azobis isobutyronitrile, and the like.

The polymerization initiators can be used singly or in combination. The initiators are suitably used in an amount of from about 0.001 to about 1.0 weight percent, preferably from about 0.01 to about 0.5 weight percent based on the total weight of monomer present in the oil-in-water suspension.

Those skilled in the art will recognize suitable conditions under which the polymerization of the water-soluble monomers can be carried out. As a general rule the polymerization is initiated at a temperature within the range of from about 25° C. to about 90° C.

Polymerization of the water-soluble monomers produces a gel like mass of water-swollen water-insoluble polymeric material having dispersed therein discrete drops of the volatile organic compound. The resultant mass of polymerized material is then subjected to a drying process. As described above, the drying process occurs at a temperature and pressure such that at least a portion of the water present in the gel-like mass is evaporated prior to the time the volatile organic compound volatilizes. As discussed above the water-swollen polymeric material must dry to a degree sufficient to impart the necessary structural integrity to maintain the porous structure once the volatile organic compound volatilizes. Similarly, if the water-swollen polymeric material dries to too great an extent before volatilization occurs the desired pore structure is not formed because the polymer is generally inelastic and prevents formation of a chamber. In such a case, the volatile organic liquid is gradually released by diffusion without creating a chamber (pore), but instead forms an interior void. Such interior voids are not within the scope of the present invention.

It is to be understood that the above described method is not the only method by which the polymeric material of the present invention can be formed. Alternatively, it may be possible to form the polymeric material in the presence of a solid dispersed phase, such as a diazo compound, and create the porous nature of the product through the release of nitrogen gas formed by thermal decomposition of the diazo compound. Alternatively, if the polymerization is carried out in a pressurized vessel, liquid carbon dioxide could function as the blowing agent.

The present invention can best be understood by reference to the following examples (including comparative examples). Which examples are not intended to limit, in any way, the scope of the invention as set forth in the claims.

EXAMPLES

In all of the following examples, the reported free swell capacity is determined in the following manner.

0.5 grams of the polymeric material to be tested is placed in 50 grams of an aqueous sodium chloride solution containing 1%, by weight, sodium chloride for 30 minutes with occasional stirring. The slurry of polymer and sodium chloride solution is then poured through a tared 45 mesh sieve into a tared beaker. The water swollen polymer retained by the sieve is stirred and finally shaken to remove the excess fluid. The weight of the filtrate ($W_f$) and water-swellable polymeric material ($W_p$) is then determined. The free swell capacity is calculated according to the following formula:

$$\text{Free swell capacity} = [2(50 - W_f) + 2(W_g - 0.5)] \div 2.$$

This formula is essentially an averaging technique whereby free swell capacity is determined by change in weight of water and change in weight of polymer, with the two values being averaged. This technique is believed to minimize scatter in the data.

Example 1

In order to determine the effect of varying amounts of toluene as the dispersed (oil) phase on polymer performance, a series of samples is prepared with the only difference between the samples being the amount of toluene employed as the oil phase during the polymerization process. The amount of toluene employed directly corresponds to the porosity of the final polymeric material such that the more toluene employed the greater the porosity of the resultant polymeric material.

The reaction vessel employed in the following polymerization process is an air jacketed polymerization vessel. The vessel in which the polymerization occurs is about one inch smaller in outside diameter than the inside diameter of the heating mantle. In the heating cycle, electric coils present in the mantle heat the air around the polymerization vessel. The temperature within the reaction vessel is determined by a thermister which in turn controls the heating of the polymerization vessel by the electric coils present in the mantle or the cooling of the polymerization vessel by removal of the air present in the mantle around the polymerization vessel.

The polymerization vessel cover has four standard tapered 24/40 ports for the agitator, the nitrogen inlet, condenser, and thermowell. The glass agitator shaft has a teflon paddle and bushing with O-ring seal. The shaft is connected to a constant-speed stirrer such that when the contents of the polymerization vessel become unstirrable the constant-speed stirrer is inactivated.

A nitrogen purge (100 cubic centimeters per minute) is started in the polymerization vessel. To the vessel is added 15 grams (0.375 mole) of sodium hydroxide. Next, 168.30 grams of distilled water is added to the polymerization reactor. To the resultant caustic solution is added 36 grams (0.5 mole) of acrylic acid, 0.77 grams (0.005 mole) N,N'-methylenebisacrylamide and 0.36 grams (1% by weight monomer) of polyvinyl alcohol commercially available from the E. I. Dupont de Nemours and Company, under the trade designation Elvanol 51-05. Varying amounts of Toluene are then added to the polymerization vessel. The specific amounts of Toluene added are set forth in Table 1 which follows. Sample 1 serves as a control and contains no toluene.

After addition of the toluene, the polymerization vessel is brought to 70° C. and 0.20 grams of sodium persulphate initiator dissolved in 5.0 grams of water is added to the polymerization vessel. Polymerization of the monomeric material present in the reactor continues until the formation of a gel-like mass. The gel is maintained in the polymerization vessel for approximately one hour after reaching the gel stage. The gel is then removed from the reactor and cut into small pieces. The gel is dried on a glass plate overnight in a vented 110° C. vacuum oven adjusted to 15 inches of mercury. The resultant dried polymer is ground in a laboratory blender. The ground polymer is then segregated according to particle size and the polymer passing through a 20 mesh screen and retained on a 100 mesh screen (150–850 microns) is characterized according to free-swell capacity. The results of the characterization are set forth in Table 1.

TABLE 1

| Sample Number | % Toluene[1] | F.S. Capacity[2] |
|---|---|---|
| 1* | 0 | 31.4 |
| 2 | 5 | 32.5 |
| 3 | 10 | 33.9 |
| 4 | 15 | 35.5 |
| 5 | 25 | 36.1 |
| 6 | 30 | 32.8 |

*Not an example of the present invention.
[1]Percent Toluene in weight percent based on total weight of water.
[2]Free swell capacity in grams of absorbed liquid (1% sodium chloride) per gram of dry polymer.

It is seen from reference to Table 1 that the free swell capacity increases as the percent of toluene increases, up to a maximum toluene concentration of approximately 25%. As will be seen from the examples which are to follow, improved free swell capacity can be achieved by increasing the percent of toluene above 30 weight percent. Accordingly, the fact that Sample No. 6 exhibits a lower free swell capacity indicates that there was insufficient suspending agent present in the polymerization mixture to properly suspend 30% of toluene.

Example 2

This experiment seeks to maximize the free swell capacity of the particular polymerization system set forth in connection with Example 1. Accordingly, both the amount of toluene and the amount of suspending agent (polyvinyl alcohol) were varied to locate the optimum suspending agent and toluene concentrations. The specific amounts of toluene and polyvinyl alcohol employed are set forth in Table 2. With the exception of varying the amount of toluene and polyvinyl alcohol the polymerization procedure followed is the same as that set forth in connection with Example 1.

TABLE 2

| Sample No. | % Toluene | % PVA[2] | F.S. Capacity[3] |
|---|---|---|---|
| 7* | 0 | 2.0 | 30.0 |
| 8 | 30 | 2.0 | 37.8 |
| 9 | 30 | 3.0 | 35.8 |
| 10 | 45 | 2.0 | 39.9 |
| 11 | 45 | 2.5 | 38.6 |
| 12 | 45 | 3.0 | 36.2 |
| 13 | 50 | 2.5 | 34.7 |
| 14 | 50 | 3.0 | 40.5 |
| 15 | 50 | 3.5 | 37.5 |

*Not an example of the present invention.
[1]Percent toluene in weight percent based on total weight of water.
[2]Percent polyvinyl alcohol in weight percent based on total monomer weight.
[3]Free swell capacity in grams of absorbed liquid (1% sodium chloride) per gram of polymer.

As can be seen from reference to Table 2, there is little advantage to be achieved by increasing the percent of toluene beyond approximately 45%. While a slight increase was seen by increasing the concentration of toluene to 50% the polymeric material so produced was found to possess an unsatisfactory ability to absorb water under a load of 0.3 pounds per square inch. Accordingly, for this particular polymerization system, increasing the oil phase to 50% was found to deleteriously affect the other physical properties of the polymeric material.

Example 3

When the polymeric materials of the present invention are to be incorporated into an absorbent product, such as a diaper, the polymeric material will be in contact with other absorbent materials such as a fibrous web. Thus, in order to fully appreciate the advantages of the present invention it is necessary to determine the free swell capacity of the porous polymeric materials of the present invention when such materials are in contact with an absorbent product capable of pulling fluid in the pores of the polymeric material away from the polymeric material. Accordingly, the ability of a porous polymeric material according to the present invention to retain liquid while in contact with an absorbent material is compared to the ability of a non-porous polymeric material to retain fluid while in contact with an absorbent material.

Sample No. 7 from Table 2 was employed as the non-porous polymeric material with Sample No. 10 from Table 2 being employed as the porous polymeric material. After the free swell capacity of the two samples is determined in accordance with the procedure set forth above, the swollen polymeric materials are sandwiched between cellulosic paper toweling commercially available from the Kimberly-Clark Corporation under the trade designation HI-DRI ®. The samples so treated are then weighed and dried overnight in a 100° C. convection oven. The moisture content of the blotted samples and the dried samples is then determined by difference after adjusting for the weight of residual sodium chloride. The results of this experiment are set forth in Table 3.

TABLE 3

| Sample No. | % Toluene | % PVA | F.S. Capacity | Retention Capacity[1] |
|---|---|---|---|---|
| 7* | 0 | 2.0 | 30.0 | 27.7 |
| 10 | 45 | 2.0 | 39.9 | 32.0 |

*Not an example of the present invention.
[1]Retention capacity on cellulose in grams of fluid per gram of polymer after blotting on cellulose toweling.

As can be seen from Table 3, the retention capacity of the porous polymeric material of the present invention is improved compared to the solid polymeric material even after blotting on a cellulose toweling.

Figure 2:
Figure 3:
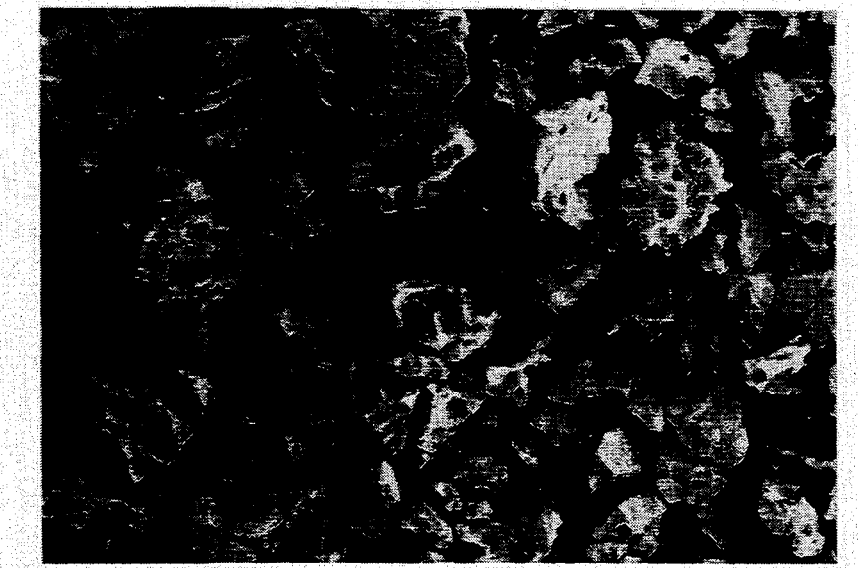
FIGS. 3 and 4 are photomicrographs of the porous water-swellable polymeric materials of the present invention.
Figure 4:

Photomicrographs were taken of Samples number 7 and 10 to visually confirm the porous nature of the materials according to the present invention. FIGS. 1 and 2 are photomicrographs of Sample 7 showing the nonporous nature of the polymeric material. FIG. 1 is at 20 times magnification, FIG. 2 is at 100 times magnification. Sample 7 is representative of known, nonporous polymeric absorbents. FIGS. 3 and 4 are photomicrographs of Sample 10 revealing the porous nature of the polymeric materials of the present invention. FIG. 3 is at 20 times magnification. FIG. 4 is at 100 times magnification.

Example 4

The free swell rate of the porous polymeric material of the present invention is also improved compared to the free swell rate of non-porous polymeric material. Again, Sample No. 7 from Table 2 is employed as the control sample of non-porous polymeric material with Sample No. 10 from Table 2 being employed as the porous polymeric material according to the present invention. The free swell capacity of the two polymeric materials is determined as a function of time. The results of the free swell rate determination comparison is set forth in Table 4.

TABLE 4

| | Free Swell Capacity[1] Time (sec.) | | | | | |
|---|---|---|---|---|---|---|
| Sample No. | 15 | 30 | 60 | 120 | 180 | 240 |
| 7* | N.D. | 9.1 | 14.6 | 18.8 | N.D. | 20.1 |
| 10 | 9.4 | 18.8 | 25.4 | 30.4 | 35.7 | 38.6 |

*Not an example of the present invention
N.D. means not determined
[1]Free swell capacity in grams of liquid (1% sodium chloride) per gram of polymer as a function of time in seconds.

Figure 5:
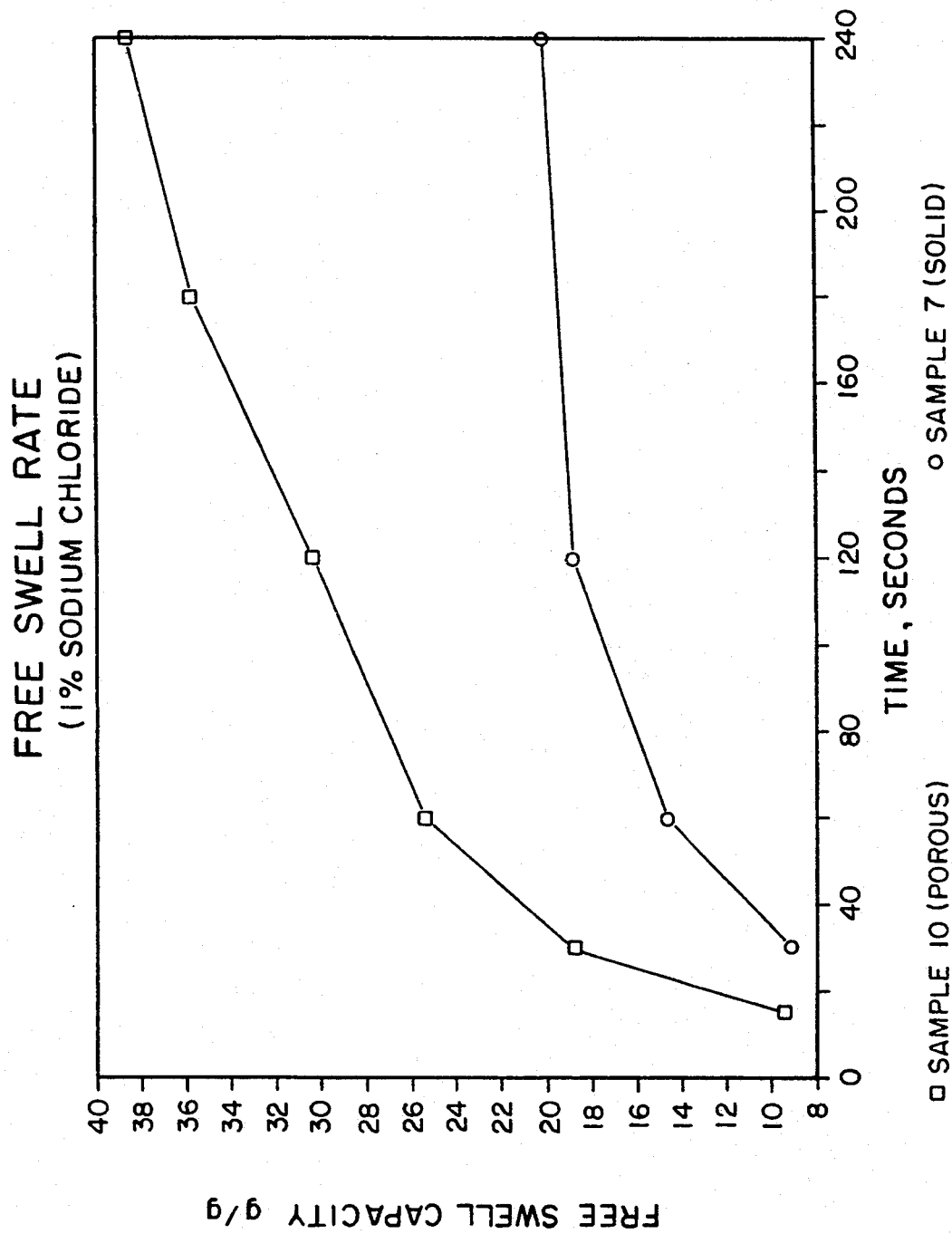
FIG. 5 is a graphic representation of the data set forth in Table 4.

As can be seen from Table 4, the free swell rate of the porous polymeric material of Sample No. 10 is greater than the free swell rate of the non-porous material of Sample No. 7. The free swell rates are represented by the slope of the lines appearing in FIG. 5 which is a graphic representation of the data set forth in Table 4.

Moreover, as can be seen from Table 4, at the end of 240 seconds (4 minutes) the porous polymeric material of Sample No. 10 has achieved approximately 97% of its 30 minute free swell capacity while the non-porous sample (No. 7) has achieved only about 67% of its 30 minute free swell capacity.

As is apparent from the foregoing specification, the present invention is susceptible of being embodied with various alterations and modifications which may differ particularly from those that have been described in the preceding specification and description. For this reason, it is to be understood that all of the foregoing is intended to be merely illustrative and is not to be construed or interpreted as being restrictive or otherwise limiting of the present invention, excepting as it is set forth and defined in the following claims.

What is claimed is:

1. A process for forming a porous particle of a water-swellable, water-insoluble polymeric material, the process comprising the following steps:
    (a) forming an oil-in-water suspension, the water phase containing at least one water-soluble monomer and a crosslinking agent, the oil phase comprising a volatile organic compound having a boiling point greater than the boiling point of water;
    (b) polymerizing the monomer present in the water phase to form a water-swellable, water-insoluble polymeric material having dispersed therein the oil phase and;
    (c) drying the water-swellable, water-insoluble polymeric material at a temperature above the boiling point of water such that the volatile organic compound volatilizes to form chambers having a diameter of at least 20 microns, said chambers being in open communication with an ambient atmosphere wherein the polymeric material is at least partially dried before the organic compound volatilizes.

2. The process according to claim 1 wherein said water-soluble monomer is present in said water phase in an amount of from about 15 to about 50 weight percent based on total weight of the water.

3. The process according to claim 2 wherein said crosslinking agent is present in said water phase in an amount of from about 0.01 to about 5.0 weight percent based on total weight of the monomer.

4. The process according to claim 1 wherein the water-soluble monomer is selected from the group consisting of vinyl monomers having a polymerizable unsaturated group and the water soluble salts of said monomers.

5. The process according to claim 1 wherein the volatile organic compound is selected from the group consisting of toluene; 1-butanol; 1,1-dimethylcyclohexane; and octane.

6. The process according to claim 5 wherein the volatile organic compound is present in an amount of from about 10 weight percent to about 40 weight percent based on total weight of the oil-in-water suspension.

7. The process according to claim 1 wherein the water phase further comprises a suspending agent.

8. A porous polymeric particle formed by the process according to claim 1.

* * * * *